(12) United States Patent
Haex et al.

(10) Patent No.: US 7,899,220 B2
(45) Date of Patent: Mar. 1, 2011

(54) TIME-DEPENDENT THREE-DIMENSIONAL MUSCULO-SKELETAL MODELING BASED ON DYNAMIC SURFACE MEASUREMENTS OF BODIES

(75) Inventors: Bart Maria Jozef Haex, Leuven (BE); Jozef Vander Sloten, Boortmeerbeek (BE); Helmut Diers, Schlangenbad (DE); Kjell Roger Heitmann, Wiesbaden (DE)

(73) Assignee: DIERS International GmbH, Schlangenbad (DE)

( * ) Notice: Subject to any disclaimer, the term of this patent is extended or adjusted under 35 U.S.C. 154(b) by 1162 days.

(21) Appl. No.: 10/590,598

(22) PCT Filed: Feb. 25, 2005

(86) PCT No.: PCT/BE2005/000031

§ 371 (c)(1),
(2), (4) Date: Aug. 24, 2006

(87) PCT Pub. No.: WO2005/082249

PCT Pub. Date: Sep. 9, 2005

(65) Prior Publication Data

US 2007/0171225 A1    Jul. 26, 2007

(30) Foreign Application Priority Data

Feb. 26, 2004    (GB) .................... 0404269.3

(51) Int. Cl.
*G06K 9/00* (2006.01)
(52) U.S. Cl. ..................... 382/128; 382/154
(58) Field of Classification Search ............ 382/128, 382/130, 154
See application file for complete search history.

(56) References Cited

U.S. PATENT DOCUMENTS

| 5,625,577 | A | 4/1997 | Kunii et al. |
| 6,373,963 | B1 | 4/2002 | Demers et al. |
| 2002/0009222 | A1 | 1/2002 | McGibbon et al. |
| 2002/0031265 | A1* | 3/2002 | Higaki ................. 382/199 |

OTHER PUBLICATIONS

Written opinion of the International Searching Authority (dated Oct. 13, 2005).
International Search Report (dated Oct. 13, 2005).
Response to Written Opinion for PCT/BE2005/000031 (dated Jan. 13, 2006).
International Preliminary Report on Patentability (dated Jun. 2, 2006).

(Continued)

*Primary Examiner*—John B Strege
(74) *Attorney, Agent, or Firm*—Clark & Elbing LLP

(57) ABSTRACT

Active contour models and active shape models were developed for the detection of the kinematics landmarks on sequential back surface measurements. The anatomical landmarks correspond with the spinous process, the dimples of the posterior superior iliac spines (PSIS), the margo mediales and the elbow. Back surface curvatures are used as a basis to guide the ACM and ASM's towards interesting landmark features on the back surface. Geometrical bending and torsion costs, and the main modes of variation of the landmark points are added to the models in order to avoid unrealistic curve shapes from a biomechanical point of view. Reconstruction of the underlying skeletal structures is performed using the surface normals as approximations for skeletal rotations (e.g. axial vertebrae rotations, pelvic torsion, etc.) and anatomical formulas to estimate skeletal dimensions.

9 Claims, 13 Drawing Sheets

OTHER PUBLICATIONS

Drerup and Hierholzer, "Automatic Localization of Anatomical Landmarks on the Back Surface and Construction of a Body-Fixed Coordinate System", J. Biomechanics 20: 961-970, 1987.

Drerup and Hierholzer, "Back Shape Measurement Using Video Rasterstereography and Three-Dimensional Reconstruction of Spinal Shape", Clin. Biomech. 9:28-36, 1994.

Kervrann et al., "A Hierarchical Markov Modeling Approach for the Segmentation and Tracking of Deformable Shapes," Graphic Models and Image Processing 60(3):173-195 (1998).

Nadia Magnenat-Thalmann, Hyewon Seo, Frederic Cordier, "Automatic Modeling of Animatable Virtual Humans—A Survey," 3dim, p. 2, Fourth International Conference on 3-D Digital Imaging and Modeling (3DIM '03), 2003.

Plankers et al., "Automated Body Modeling from Video Sequences," Modelling People, 1999. Proceedings. IEEE International pp. 45-52 (1999).

Proesmans et al., "Active Acquisition of 3D Shape for Moving Objects," IEEE 647-650 (1996).

"Proceedings IEEE International Workshop on Modelling People. Mpeople' 99" Modelling People, 1999. Proceedings. IEEE International Workshop on Kerkyra, Greece Sep. 20, 1999, Los Alamitos, CA, USA, IEEE Comput. Soc, US , 1999.

Rohr, "Extraction of 3D anatomical point landmarks based on invariance principles," Pattern Recognition 32:3-15 (1999).

Zhang, Brian Curless, and Steven M. Seitz. Rapid Shape Acquisition Using Color Structured Light and Multi-pass Dynamic Programming. In Proceedings of the 1st International Symposium on 3D Data Processing, Visualization, and Transmission (3DPVT), Padova, Italy, Jun. 19-21, 2002, pp. 24-36.

L. Zhang, B. Curless, and S. M. Seitz. Spacetime Stereo: Shape Recovery for Dynamic Scenes. In Proceedings of IEEE Computer Society Conference on Computer Vision and Pattern Recognition (CVPR), Madison, WI, Jun. 2003, pp. 367-374.

EPO Communication for European Application No. 05 706 375.2-2319 (Dated Mar. 19, 2010).

Reply to EPO Communication dated Mar. 19, 2010, for European Application No. 05 706 375.2-2319 (Reply dated Jul. 8, 2010).

\* cited by examiner

TIME-DEPENDENT THREE-DIMENSIONAL MUSCULO-SKELETAL MODELING BASED ON DYNAMIC SURFACE MEASUREMENTS OF BODIES

CROSS-REFERENCE TO RELATED APPLICATIONS

This application is the U.S. National Stage of International Application No. PCT/BE2005/000031, filed Feb. 25, 2005, which, in turn, claims the benefit of British Patent Application Serial No. 0404269.3, filed Feb. 26, 2004.

TECHNICAL FIELD OF THE INVENTION

The invention relates to a system and method for time-dependent three-dimensional measurement and functional analysis of bodies. In particular the invention relates to a system and method for obtaining a time-dependent and three-dimensional musculo-skeletal system for bodies or body parts. The invention furthermore relates to a system and method for quickly and accurately detecting landmarks on three-dimensional and time-dependent images of body parts and to a system and method for constructing a feasible or approximate musculo-skeletal model based on three-dimensional and time-dependent images of body parts.

BACKGROUND OF THE INVENTION

The amount of people suffering from different musculo-skeletal complaints, such as back pain or knee problems, is large. As a consequence, orthopaedic physicians and physiotherapists are required to analyse a variety of movements of the body to diagnose pathological or abnormal changes. Up to now, time-dependent three-dimensional recordings of movement under functional conditions are not possible with conventional techniques. As an ersatz, one or more three-dimensional scans (e.g. RX) of selected body parts, such as e.g. knees or feet, are made under given conditions, such as e.g. bending of the limbs/extension, i.e. stretching, of the limbs, or video-based kinematographic methods, such as e.g. marker tracing are used to calculate kinematical parameters, i.e. for example for gait analysis. An overview of the history and technical constraints and different available systems is given by D. H. Sutherland in "The evolution of clinical gait analysis. Part II Kinematics", Gait and Posture (2002), 16, 159-179.

US Patent application US 2002/0009222 A1 describes a method for determining kinetic and kinematic information for a 3D image of a human body. It is based on an input device for images, a transformation system to obtain 3D information and a system for obtaining kinematic and kinetic information. The image input is based on information of markers placed on the object. This information is transformed into a 3D image based on an anatomical coordinate system of the body segment. Finally the positions and orientations are computed in global space for dynamical images. US 2002/0009222 does not provide a non-contact technique for obtaining information and furthermore does not use muscular modelling. The application of landmark markers to the body is time consuming and must be tolerated by patients.

U.S. Pat. No. 6,169,817 B1 describes a system and method for 4D kinematic reconstruction and visualization of body tissue. The method is based on segmenting a 3D image, following the motion of the different segments, e.g. based on finite element models and using the detailed four-dimensional representation of bone, muscles, skin and other tissue as a digital clone to study the motion and biomechanical properties. The document describes the construction of a model based on expensive techniques and involving potentially harmful techniques which require careful management.

In "4D analysis of muscular dynamics using flexible 3D muscle models", International Conference on Artificial Reality and Telexistence '99, Suziki et al. describe a method for constructing a 4D musculo-skeletal model. The method is based on fitting a muscular and skeletal model to MRI results and measuring movement by a video camera and a set of sensors.

The above-mentioned documents describe the construction of a biomechanical model based on expensive techniques and potentially harmful medical techniques which require careful control to maintain proper patient care. Furthermore, the methods described in the above mentioned documents have the disadvantage that the computing power needed for time-dependent detection of landmarks on time-dependent images of body parts can be high. The above mentioned documents furthermore have the disadvantage that a musculo-skeletal model only can be obtained based on images of the interior of the body parts. Furthermore, the above mentioned documents have the disadvantage that the musculo-skeletal model obtained can lead to bio-mechanical inconsistent features and that the computing power for obtaining the musculo-skeletal model is large. Due to the large computing power needed, the systems and methods for obtaining a musculo-skeletal model are tedious and labour-intensive.

SUMMARY OF THE INVENTION

It is an object of the present invention to provide a method and system for efficiently obtaining a dynamical 3 dimensional musculo-skeletal model for parts of a body.

It is a further object of the present invention to provide a method and a system for efficiently detecting landmarks on a time-dependent 3 dimensional image of the surface of parts of a body.

It is a further object of the present invention to provide a method and a system for efficiently creating a musculo-skeletal model that complies with bio-mechanical restraints.

It is a further object of the present invention to provide a method and a system for efficiently creating a musculo-skeletal model that uses less potentially harmful techniques for a patient.

The above objectives are accomplished by methods and devices according to the present invention.

The invention relates to a computer based method for obtaining a musculo-skeletal model of at least part of the body of a creature from a series of time-dependent optical 3 dimensional images of a surface of said at least part of a body of a creature. The method comprises detecting anatomical surface information based on a topography of the surface in said series of time-dependent optical 3 dimensional images of the surface of said at least part of a body of a creature and reconstructing internal structures based on said detected anatomical surface information. The anatomical surface information may be anatomical landmarks and/or the shape of the surface. The series of time-dependent optical 3 dimensional images of a surface of at least part of a body of a creature may be provided by a non-contact and non-invasive scanning method. For example, it may be provided by an optical method such as structured light projection. The series of time-dependent optical 3 dimensional images of a surface of at least part of a said body of a creature may furthermore be provided using raster line triangulation. The series of time-dependent optical 3 dimensional images of a surface of at least part of a body of a creature may be provided using stereoscopic techniques. The series of time-dependent optical 3 dimensional images of a surface of at least part of a body of a creature may also be provided by obtaining said 3 dimensional images whereby each of a width, height and depth of said 3 dimensional images can have a length up to at least 1.2 m. The series of time-dependent optical 3 dimensional images of a surface of at least part of a body of a creature may also be provided by using a multi-view system. Detecting anatomical surface information based on the topography of the surface in said series of time dependent optical 3 dimensional images may be obtained by active contour modelling. The active contour modelling may be based on optimising a finite number of active contour points, whereby all active contour points substantially being at an equal distance. Detecting anatomical surface information based on the topography of the surface in said series of time-dependent optical 3 dimensional image may be obtained by active shape modelling. Reconstruction of internal structures may comprise at least one of the group of bones, ligaments, tendons and muscles. The reconstruction may be topographically or topologically correct.

The invention also relates to a method for collecting data suitable for diagnostics of disorders in bodies of creatures, comprising building a computer based musculo-skeletal model obtained according to a method as described above.

The invention also relates to a system for obtaining a musculo-skeletal model of at least part of a the body of a creature, the system comprising means for providing a series of time-dependent optical 3 dimensional images of the surface of said at least part of the body of a creature, means for detecting anatomical surface information on said series of time dependent optical 3 dimensional images of a surface of said at least part of a body of a creature and means for reconstructing internal structures based on said detected anatomical surface information. Said anatomical surface information may be anatomical landmarks. The means for providing a series of time dependent optical 3 dimensional images of the surface of said at least part of the body of a creature may comprise means for obtaining optical 3 dimensional images of a surface of said at least part of a body of a creature.

The invention furthermore relates to a computer based method for detecting and/or extracting, from a series of time-dependent images of a surface of body parts of a creature, anatomical features on surface measurements, said method comprising using invariant feature analysis to determine anatomical surface information and shapes, wherein said invariant feature analysis comprises fulfilling predetermined conditions describing topographic characteristics of the surface of the body parts of a creature and fulfilling predetermined conditions describing topographic, topologic and/or volumetric characteristics of the interior of the body parts of a creature. The topographic characteristics of the surface of the body parts of a creature may be at least one of curvature and symmetry of surface parts of the body parts of a creature and wherein the topographic, topologic and/or volumetric characteristics of the interior of the body parts of a creature may be at least one of the relative position, bending, torsion, equidistance and dynamical properties of interior parts of the body parts of a creature. The topographic characteristics of the surface of the body parts of a creature may be all of curvature and symmetry of surface parts of the body parts of a creature and the topographic, topologic and/or volumetric characteristics of the interior of the body parts of a creature may be all of the relative position, bending, torsion, equidistance and dynamical properties of interior parts of the body parts of a creature. The predetermined conditions describing topographic characteristics of the surface of the body parts of a creature and the predetermined conditions describing topographic, topologic and volumetric characteristics of the interior of the body parts of a creature may be determined by biomechanical constraints.

The present invention also relates to a system for detecting and/or extracting anatomical features on surface measurements. Said system comprises means for providing a series of time-dependent images of a surface of body parts of a creature, and means for determining anatomical surface information, wherein the means for determining anatomical surface information are adapted for using invariant feature analysis which comprises fulfilling predetermined conditions describing topographic characteristics of the surface of the body parts of the creature and which comprises fulfilling predetermined conditions describing topographic, topologic and/or volumetric characteristics of the interior of the body parts of the creature. Said topographic characteristics of the surface of the body parts of the creature are any, i.e. at least one, or all of curvature and symmetry of surface parts of the body parts of the creature; and said topographic, topologic and/or volumetric characteristics of the interior of the body parts of the creature are any, i.e. at least one, or all of the relative position, bending, torsion, equidistance and dynamical properties of interior parts of the body parts of the creature. The system may furthermore comprise means for determining by biomechanical constraints said predetermined conditions describing topographic characteristics of the surface of the body parts of the creature and said predetermined conditions describing topographic, topologic and volumetric characteristics of the interior of the body parts of the creature.

The invention also relates to a computer program product for executing any of the methods as described above. The computer program product may include method steps for controlling illumination means for detection purposes, i.e. illumination means for providing a series of optical 3 dimensional images by carrying out structured light projection or raster line triangulation. The invention furthermore relates to a machine-readable data storage device storing that computer program product. The invention also relates to transmission of that computer program product over a local or wide area telecommunications network.

The invention also relates to a computer based method for constructing a biomechanical model of a musculo-skeletal structure of at least part of a body of a creature from time-dependent anatomical surface information, the method comprising determining from said time-dependent anatomical surface information a set of boundary conditions for a biomechanical model of a musculo-skeletal structure and fitting a bio-mechanical model of a musculo-skeletal structure according to said set of boundary conditions. The anatomical surface information may comprise both landmarks and/or surface shapes. The method furthermore may comprise initially scaling an calibrating said biomechanical model of a musculo-skeletal structure based on anatomical surface information obtained for said at least part of a body of a creature in a predefined position. The method also may comprise, after fitting a biomechanical model of a musculo-skeletal structure, checking the plausibility of said biomechanical model of a muskulo-skeletal structure with respect to biomechanical constraints. The method furthermore may comprise after fitting a biomechanical model of a musculo-skeletal structure according to said set of boundary conditions, dynamically adjusting and refining said biomechanical model of a musculo-skeletal structure by repeatedly obtaining new time-dependent anatomical surface information, determining the new boundary conditions for a biomechanical model of a musculo-skeletal structure based on said new time-dependent anatomical surface shape information and adjusting said biomechanical model of a musculo-skeletal structure according to said set of new boundary conditions.

The invention also relates to a computer program product for executing the method as described above. The invention also relates to a machine-readable data storage device storing that computer program product. The invention also relates to transmission of that computer program product over a local or wide area telecommunications network.

The invention also relates to a system for constructing a biomechanical model of a musculo-skeletal structure of at least part of a body of a creature. The system comprises input means for obtaining time-dependent anatomical surface information, first calculation means for determining from said time-dependent anatomical surface information a set of boundary conditions for a biomechanical model of a musculo-skeletal structure and second calculation means for fitting a bio-mechanical model of a musculo-skeletal structure according to said set of boundary conditions. The anatomical surface information may comprise both landmarks and surface shapes. The system may furthermore comprise calibration means for initially scaling and calibrating said biomechanical model of a musculo-skeletal structure based on anatomical surface information obtained for said at least part of a body of a creature in a predefined position. The system may also comprise, checking means for, after fitting a biomechanical model of a musculo-skeletal structure, checking the plausibility of said biomechanical model of a muskulo-skeletal structure with respect to biomechanical constraints. The system may furthermore comprise adjustment means for, after fitting a biomechanical model of a musculo-skeletal structure according to said set of boundary conditions, dynamically adjusting and refining said biomechanical model of a musculo-skeletal structure by repeatedly obtaining new time-dependent anatomical surface information, determining the new boundary conditions for a biomechanical model of a musculo-skeletal structure based on said new time-dependent anatomical surface shape information and adjusting said biomechanical model of a musculo-skeletal structure according to said set of new boundary conditions. The adjustment means may be controlled by a controller adapted to carry out the above sequence of steps.

The invention furthermore relates to a computer based method of extended modelling of kinematics, kinetics and dynamics of the musculo-skeletal system of a moving body comprising extraction of relevant parameters from the biomechanical model as described above.

The invention also relates to a computer program product for executing this method. The invention also relates to a machine-readable data storage device storing that computer program product. The invention also relates to transmission of that computer program product over a local or wide area telecommunications network.

It is an advantage of the invention that with the equipment it is possible to reconstruct kinematics, kinetics and dynamics of the musculo-skeletal system of the body, as well as to indicate and quantify pathological changes or abnormalities.

It is furthermore an advantage of the invention that no preparation time and only a short recording and analysing time are needed.

It is an advantage of the invention that it enables the full time-dependent three-dimensional measurement and functional analysis of the human body in a contact-free, non-invasive way, without the use of potentially harmful radiation. It is furthermore an advantage of the present invention that it allows the use of time-dependent three-dimensional images of the surface of part of a body for construction of a musculo-skeletal model.

It is an advantage of the present invention that, for the detection of time-dependent anatomical surface information on a series of time-dependent three-dimensional images of the surface, both detection points and characteristics of parts of the surface are used.

It is furthermore an advantage of the present invention that the time evolution of anatomical surface information and thus the characteristics of parts of the surface are used during construction of the musculo-skeletal model.

Although there has been constant improvement, change and evolution of devices in this field, the present concepts are believed to represent substantial new and novel improvements, including departures from prior practices, resulting in the provision of more efficient, stable and reliable devices of this nature.

The teachings of the present invention permit the design of improved methods and systems for constructing a musculo-skeletal model of at least part of a body.

These and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

DESCRIPTION OF ILLUSTRATIVE EMBODIMENTS

Figure 1:
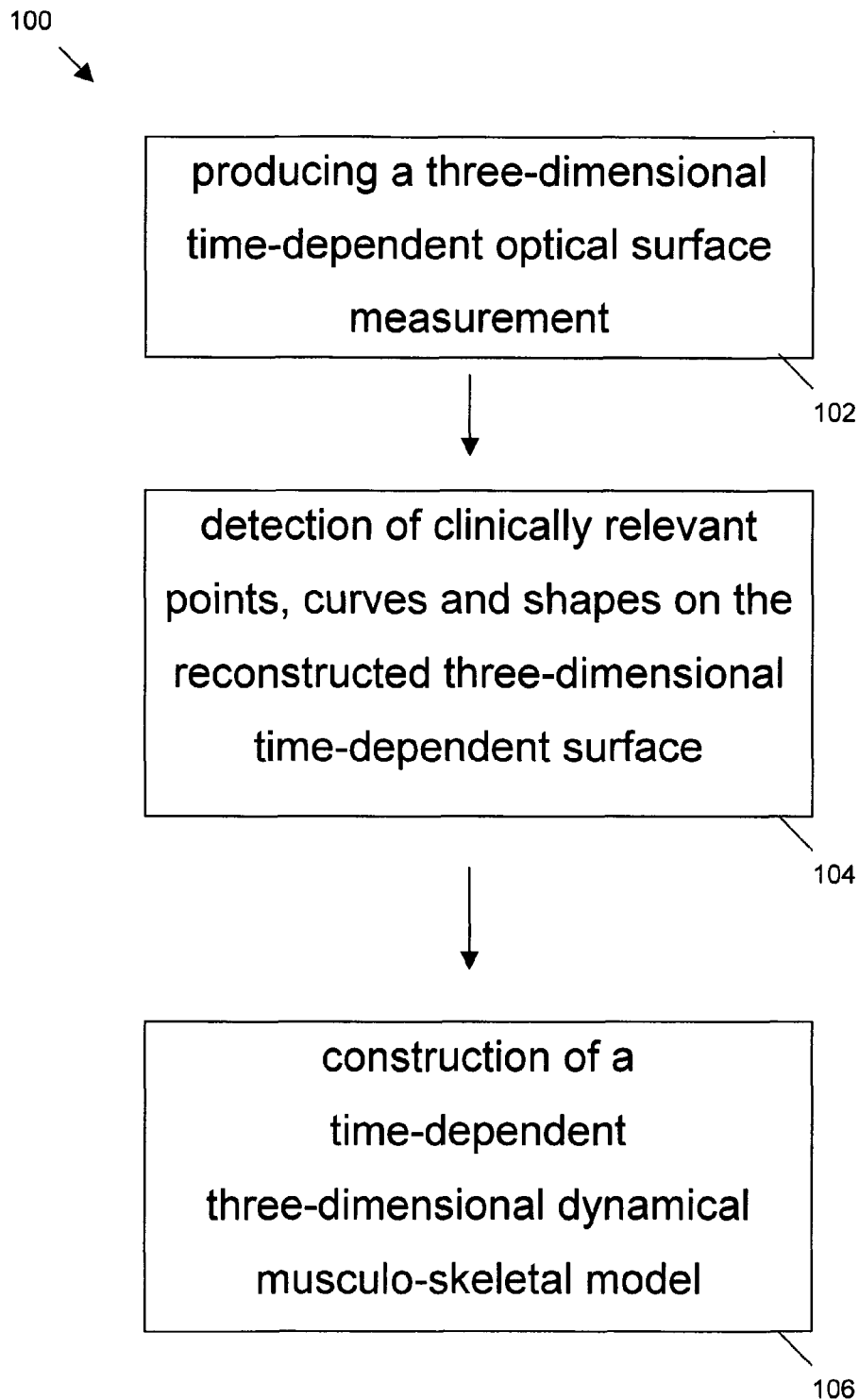
FIG. 1 is a schematic overview of the different steps of a method for constructing a musculo-skeletal model according to a first embodiment of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

In a first embodiment of the present invention, the invention relates to a method and system for obtaining a model of the internal structure of a body of a creature, e.g. of an animal or human. The model of the internal structure may be a musculo-skeletal model for a part or parts of a body. The body may be the body of a living or dead creature. The body may be the body of an animal having a skeleton and a muscle structure. The body may be the body of a mammal. The body thus also may be a human body. The body also may be an inanimate object such as a sculpture of a mammal or a plaster cast of a body, whereby the sculpture of plaster cast has surface contours representing an underlying musculo-skeletal system. In FIG. 1 a schematic overview of the different steps of the invention are illustrated. The method 100 comprises:

in a first step 102 providing images, e.g. grabbing images, of movements of part or parts of a body as a function of time and in a three dimensional representation, thus producing a dynamic three-dimensional time-dependent surface measurement, —in a second step 104, detection of clinically relevant points, areas, curves and/or shapes on the reconstructed three-dimensional time-dependent surface in an automatic way, i.e. without the use of synthetic markers attached to the surface of the body in a third step 106, construction of a time-dependent three-dimensional dynamical musculo-skeletal model to analyse and visualise clinically relevant internal structures such as e.g. bones, ligaments, tendons, muscles and to analyse and visualise body movements, constraints, dynamics, kinematics and kinetics.

The first step 102 comprises providing images, e.g. grabbing images, of movements of part or parts of a body as a function of time and in three dimensions, thus producing a dynamic three-dimensional time-dependent surface measurement. The image obtained is an image of the surface of a body. It is a specific advantage of the invention that this grabbing of movement images is performed in a contact-free way that is furthermore quick, relatively inexpensive and without risk for health. The imaging technique preferably is an optical technique. Such an optical technique may be based on visual light. The technique for imaging used may be a stereoscopic technique. The measured surface is then reconstructed mathematically, e.g. by fitting a dense point cloud, which is created based on triangulation algorithms. Other techniques of obtaining three-dimensional surface information may be used, e.g. using structured lighting.

In a second step 104 an invariant shape analysis extracts information consisting of points, curves, objects, areas and/or shapes that are anatomically relevant, e.g. the position of anatomical landmarks such as the sacrum point. Any suitable method of image analysis and pattern recognition may be used to extract anatomical surface information, such as e.g. relevant landmarks. In one preferred technique a specific (mathematical) "cost" is defined in such a way that a minimisation of the cost leads to an optimal recognition of a well defined anatomical feature, e.g. the shape of the spine. Starting from an initial estimation, a point, area, contour, object or shape is moved iteratively over the image until the cost is minimised and appropriate properties are achieved. The cost of a point, contour, area, object or shape comprises two parts: an external cost and an internal cost. The external cost guides the point, contour, area, object or shape to a minimal cost position on the surface. The internal cost describes the internal behaviour of the point, contour, area, object or shape itself, e.g. to avoid results that are impossible from a biomechanical point of view. That is the internal cost represents a constraint on the allowable values. This technique is used to detect clinically relevant points, areas, curves and shapes on the reconstructed three-dimensional time-dependent surface.

The third step 106 reconstructs an internal structure model, such as bony structures, soft tissue, ligaments and tendons in three dimensions as a function of time using musculo-skeletal models of the body. This reconstruction is based on the three-dimensional time-dependent information of the body surface itself and its features (e.g. positions of anatomical landmarks), depending on the part of the body that is scanned. Clinically relevant kinetic, kinematic and dynamic parameters are then extracted from the data. These models allow diagnostic measurements of e.g. the shape of the spine, the leg axis, foot disorders.

Figure 2:
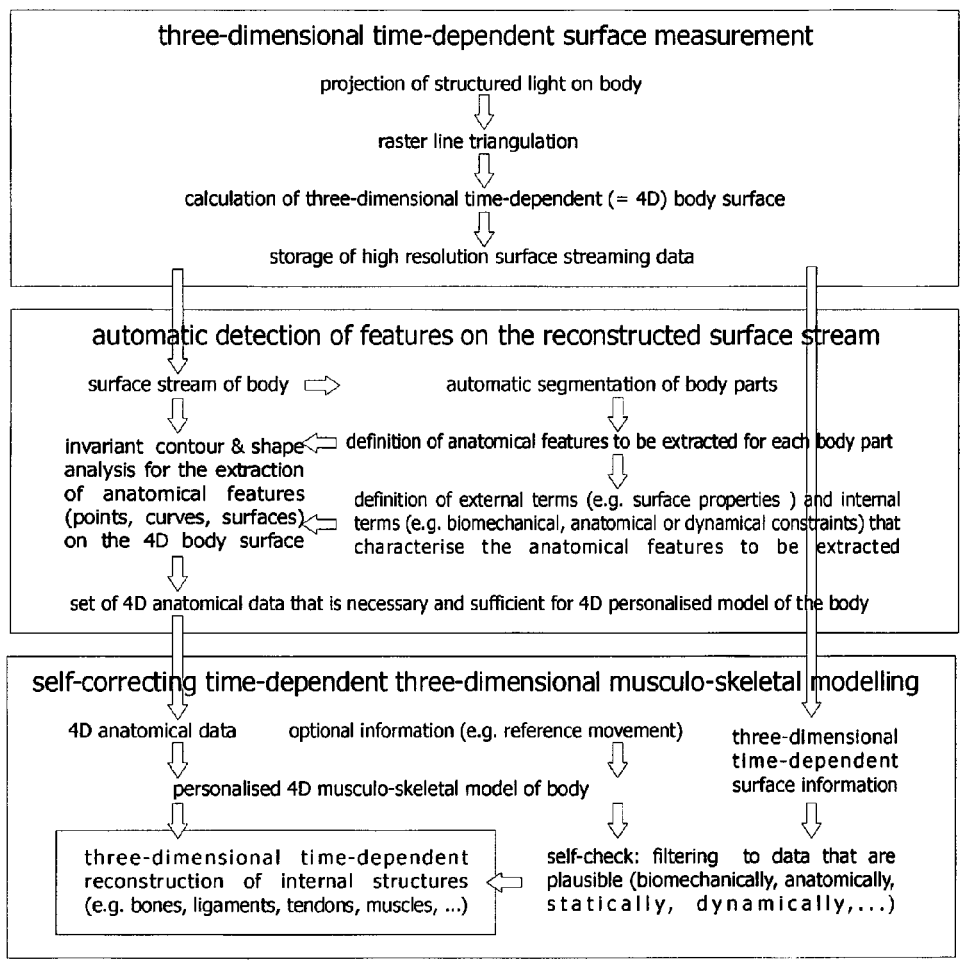
FIG. 2 is a detailed schematic overview of a preferred mode of the different steps of a method for constructing a musculo-skeletal model according to the first embodiment of the present invention.
Figure 3:
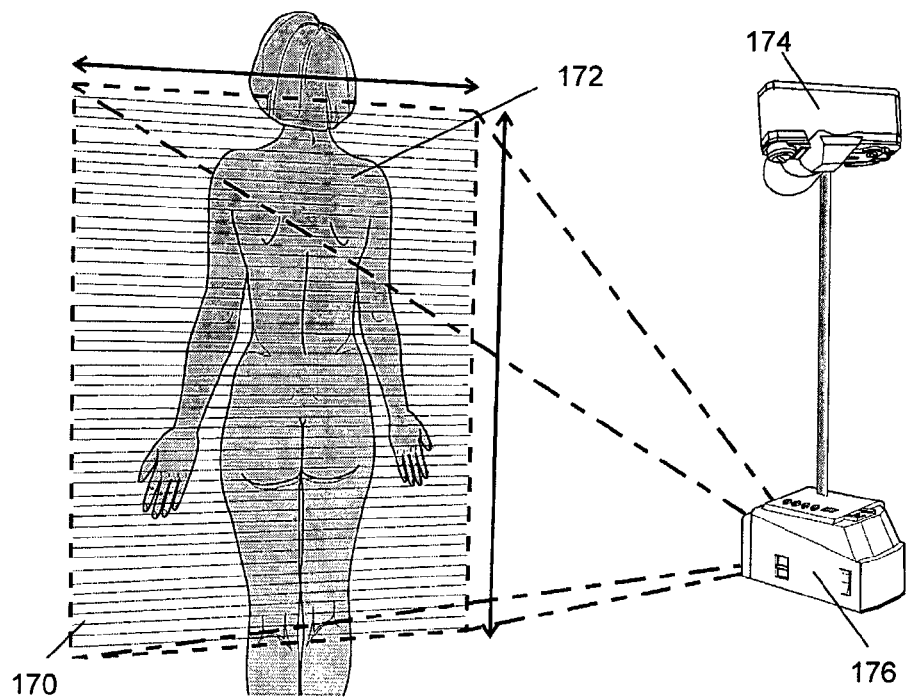
FIG. 3 is a schematical illustration of the dynamic 3 dimensional measurement of part of a body according to an embodiment of the present invention.
Figure 4:
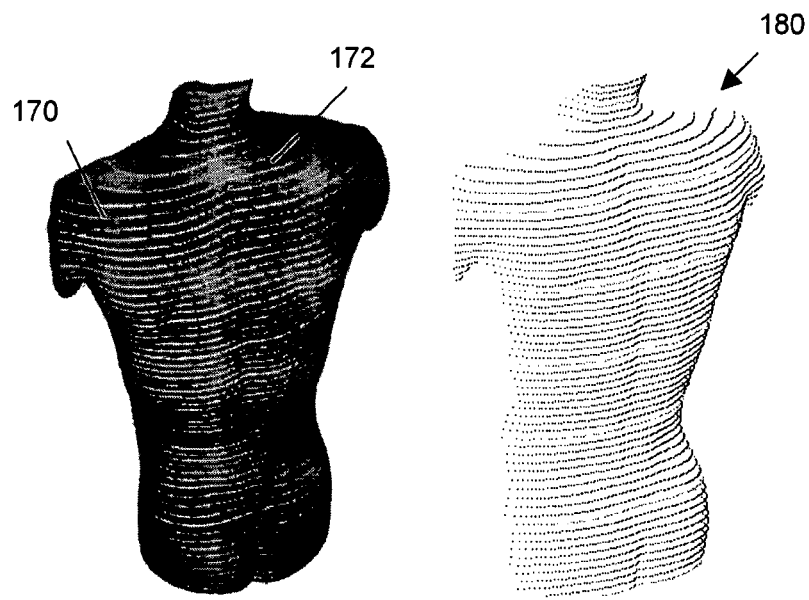
FIG. 4 is a schematic illustration of the triangulation technique applied to part of a body.
Figure 5:
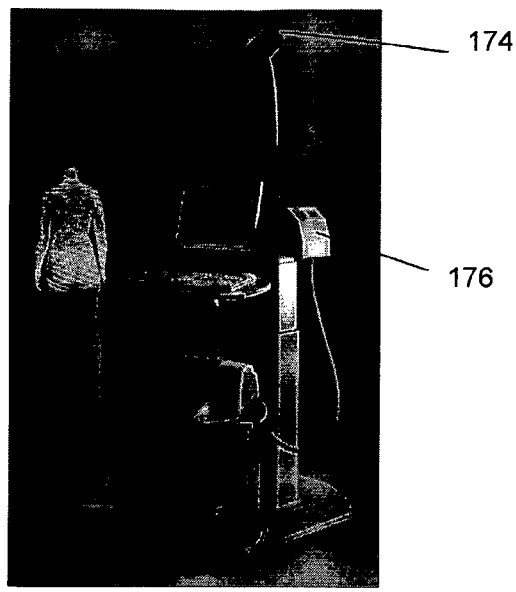
FIG. 5 is an illustration of the equipment for constructing a musculo-skeletal model for at least part of a body of a creature according to an embodiment of the present invention.
Figure 6:
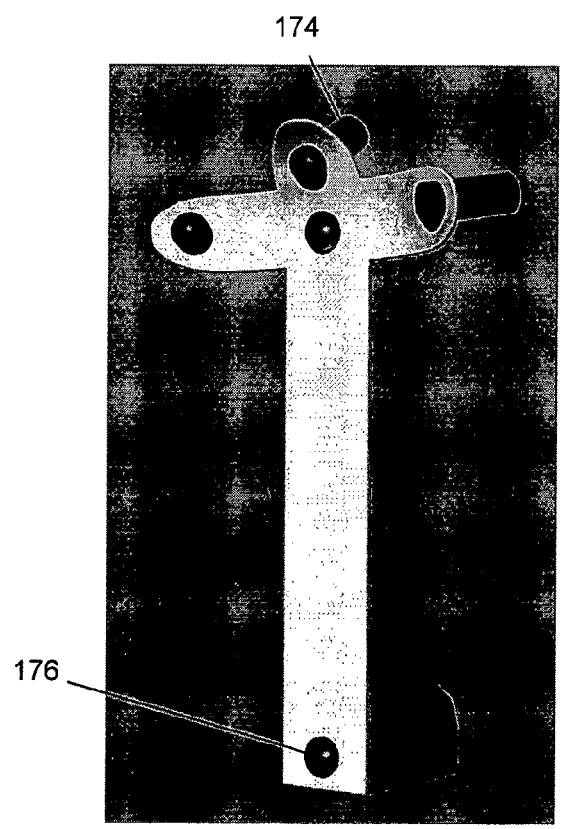
FIG. 6 is an illustration of the equipment for obtaining time dependent three-dimensional images of at least part of a body of a creature according to a preferred embodiment of the present invention.
Figure 7:
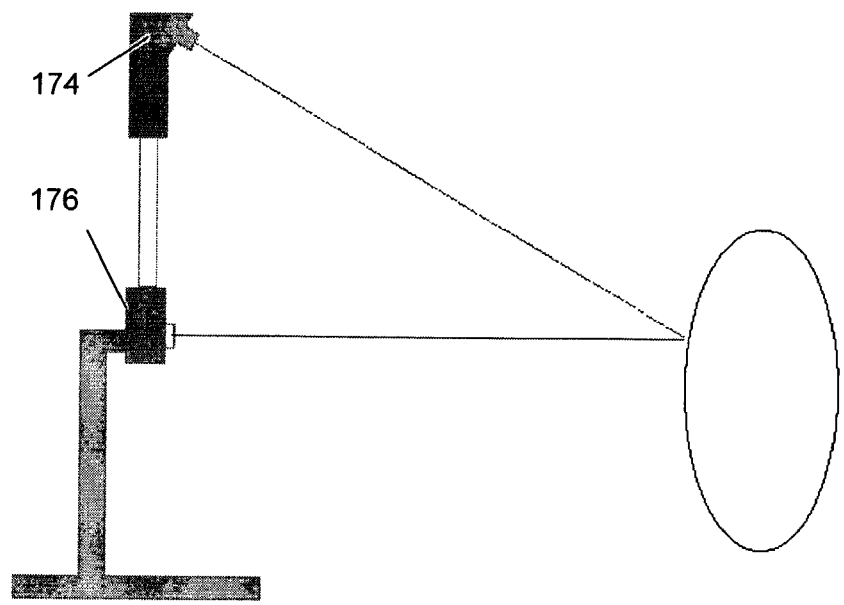
FIG. 7 is a schematic representation of the stereo basis for illumination/detection of the equipment for obtaining time dependent three-dimensional images of at least part of a body of a creature according to a preferred embodiment of the present invention.
Figure 8:
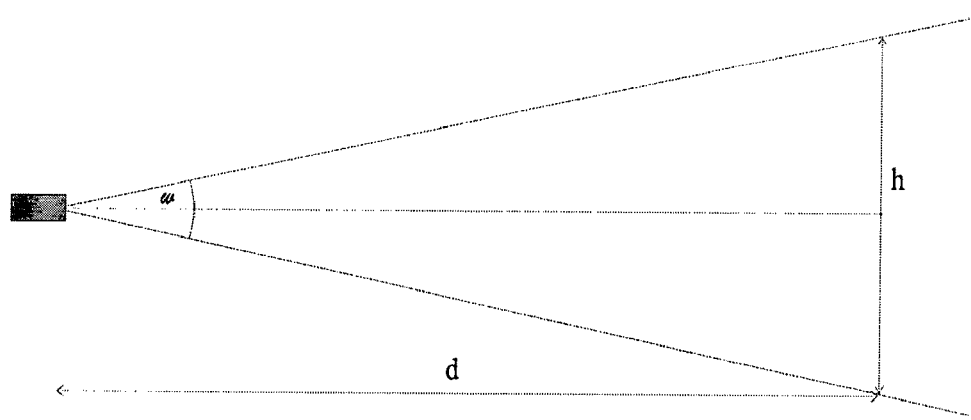
FIG. 8 is a diagram of the correlation between projection angle, height of the scanning field and distance of the mid focal plane to the projector according to the illumination/detection in a preferred embodiment of the present invention.

The method and system of the invention will be described in more detail for a preferred embodiment. The preferred embodiment of this method according to the first embodiment of the present invention comprises the different steps of method 150, as shown in FIG. 2, for constructing a biomechanical model of a musculo-skeletal structure of at least part of a body of a creature. The preferred imaging technique used during the first step—i.e. the grabbing of images of movements of the body in three dimensions as a function of time—is structured light projection combined with raster line triangulation. The invention enables the recording of a part of a body surface in three dimensions as a function of time by projecting raster lines 170, e.g. a set of parallel stripes, on the body surface 172 and by capturing these lines under a known and fixed angle with a camera 174, as illustrated in FIG. 3. In other words, a light source 176 projects a raster 170, i.e. a set of parallel stripes, on the body surface 174. The raster 170 can be a pattern of thick and thin lines. When falling onto a surface to be imaged, the stripes generate a deformed pattern 180 on the object as shown in FIG. 4, which is recorded by a camera 174, defining a fixed angle with the light source 176, e.g. projector. It is not necessary to know the fixed angle nor the distance to the object to be imaged if the system is calibrated at the required distance and at the fixed angle. The camera 174 may be at a known distance from the light source 176, e.g. by using the intersection of two lights beams at a specific distance. FIG. 5 to FIG. 7 are other illustrations of the illumination system used. The camera 174 used can be any type of camera, but typically is a digital video camera. The principle thus is to continuously project a set of parallel stripes, i.e. "raster lines" 170, on the body and with the video camera record the deformed pattern 180. The deformed pattern 180 that enables a reconstruction of the surface is created from the known or calibrated angle and known or calibrated distance between the projecting equipment, i.e. light source 176, and the recording equipment, i.e. camera 174. The light source 176 projecting the raster lines 170 on the body may be a standard white light slide-projector with a special constructed raster-line slide, consisting of lines only. The diverging angle of the projected image should preferably be low. The advantage of using this light source 176 is that it is not very expensive, as standard slide projectors may be used. The disadvantage of white light projection is the relative small focus field, which typically is in the range of 20 cm to 50 cm, as well as the sensitivity to false light. An alternative approach is to use laser projectors that are able to split a laser beam in a set of parallel lines, e.g. by using diffractive optics. Different laser projectors can be used. An example is a 685 nm, low-energy—i.e. 50 mW—laser sources with diffractive optics that split the beam in e.g. 65-130 stripes. Where lasers are used protection for the eyes of the person or animal preferably should be provided. A band-pass filter can be used on the video camera to enhance the stripes. The main advantage of the use of laser projectors is the extended focus field, i.e. between 75 cm and 150 cm, as well as the reduced weight and volume of the equipment itself. The disadvantage is a slightly more expensive system and a slightly more difficult method for sorting out the projected stripes. In case of white light projection, the system is able to capture anatomical surface data within a recording range of, for example, 1.2×1.2×0.4 m, due to the small focus area; in case of laser light projection, this range is at least a cube of 1.2×1.2×1.5 m. The accuracy of the scanned surface is high in both the laser and the white light case, i.e. a resolution smaller than 1 mm is obtained, and this is sufficient to map and preserve the features of the body to the surface, allowing detecting of surface properties and anatomical features as performed in step 2 of the method. A practical range of a low-energy time-dependent system, i.e. using laser or white light, is 50-250 cm. Longer distances require more energy to illuminate the raster lines sufficiently. Shorter distances may be used but these restrict the focus field (short distance~small focus field). A typical projection angle (between projection path and the image path to the camera) normally lies between 20° and 30°. A smaller angle than 20° may create some unwanted results due to the fish-eye effects, i.e. caused by deformation of lines, and a bigger angle may restrict the scan field unnecessary, as a long focal length results in a small field of view. For both the laser and the white light systems, a typical projector angle can e.g. be 22.5 degree. The height of the resulting scan field depends on where to define the focal mid-plane, i.e. the plane where the system is optimally focused. For the example given, i.e. a projection angle of 22.5°, the height of the resulting scan field can be calculated as h=2d tan(22.5°/2), where d is the distance from the projector to the focal mid plane. This is also shown in FIG. 8. Table 1 gives an overview of the corresponding height of the resulting scan field for different distances from the projector to the focal mid plane.

TABLE 1

| Distance from the projector to the focal mid plane | Height of the resulting scan field |
| --- | --- |
| 50 cm | 19.9 cm |
| 100 cm | 39.8 cm |
| 200 cm | 79.6 cm |
| 250 cm | 99.5 cm |

Figure 9:
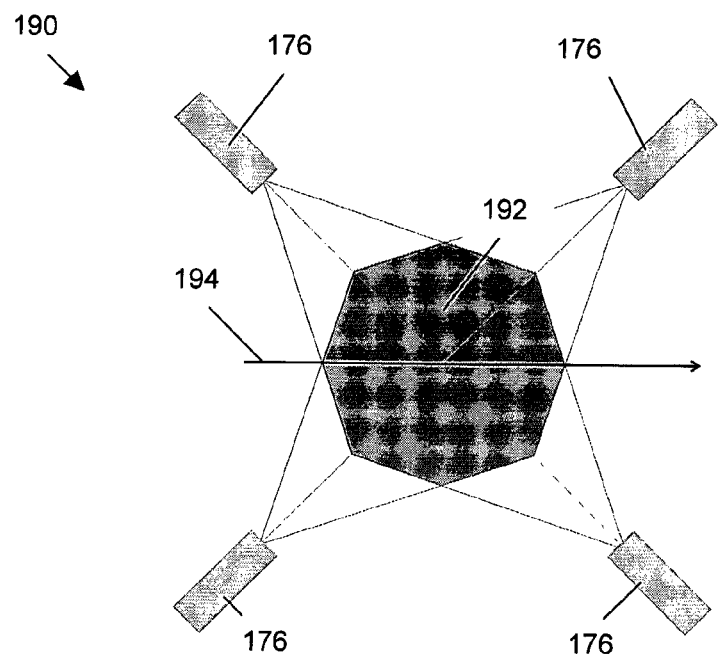
FIG. 9 is a schematic illustration of a multi-view setup for obtaining a musculo-skeletal model of part of a moving body according to an alternative embodiment of the present invention.

The width of the scan field is typically about 75%-100% of its height; due to the slightly rectangular shape of a slide, e.g. if white light is used, or the refractor optics, e.g. if a laser is used. The depth field depends on the focal length, aperture, and whether white light or laser is used. The distance between the transmitting equipment, i.e. for example a laser or white light projector and the recording/receiving equipment, i.e. for example a video camera, is defined by the distance to the scan field and the angle between transmitter and receiver. As discussed above, this angle can be determined by trial-and-error; experience shows that an angle between 20° and 45° is acceptable. A too flat angle (<20°) makes it difficult to calculate the depth values from the deformed pattern, as the degree of deformation will be low with a small angle and thus the robustness and stability of the reconstruction may suffer. Small errors in the stripe detection thus are magnifying themselves due to small deformation "tolerance" of the pattern. On the other hand, a too big angle makes the focal plane of the video camera "lean" too much, and it is difficult to get the whole body focused at one time, as the focal plane of the camera is tilted with the same degree as the camera is tilted to the projector. The use of mirrors for redirecting the field of view may open the possibility for using bigger angles, on the costs of mechanical stability and with the loss of illumination intensity. During imaging, either a one-sided surface, for example for a human the back or the face, or a multi-sided surface, for example for legs or a torso, can be imaged. When the three-dimensional time-dependent surface needs to be reconstructed from more than one side—i.e. typically when the reconstruction needs to be performed over an angle of more than 100°, e.g. in case of the analysis of the upper leg, a multi-view system 190 can be used as shown in FIG. 9, which allows measurement in a scanning area 192 for a creature moving in the direction indicated with arrow 194. The working distance of the system typically is in the range of +/−2 m.

The measured surface is then reconstructed mathematically, e.g. by fitting a dense point cloud, which is created based on triangulation algorithms, thus obtaining a sequence of single static surfaces. Based on triangulation algorithms, spatial co-ordinates of all raster points are calculated for each frame, resulting in a dense point cloud image 200 of randomly distributed points, indicating the raster lines and describing the measured surface, as illustrated on FIG. 10. Using one-dimensional linear interpolation, i.e. for example bi-linear interpolation, the randomly distributed data points are transformed to a regular grid 210, describing the body surface, as shown in FIG. 11. In other words, a frame grabber projects the digitised image on the computer screen, and the raster lines of each frame are traced and reconstructed mathematically by light intensity peak detection and line sequence analysis respectively. Artefacts and blur can be removed before this analysis. This technique is able to grab a surface in a very short time interval (<$1/100$ sec) with a high resolution (<1 mm). No special designed computer hardware is needed for the equipment, i.e. standard commercially available personal computers or laptops can be used. The computer should preferably fulfil some minimum configuration requirements; especially a relative large amount of RAM is preferred, as the digital interface to the video camera is directly connected with the RAM (the image sequence is read into RAM and "flushed" to the hard disk when the RAM is full). Any suitable operating system may be chosen of which Windows XP® supplied by Microsoft Corp. is only one option. The operating system should preferably be compatible with the digital camera interface, i.e. in principle any operating system that is compatible with the digital camera interface can be used. Additionally, a projector, which can provide white light or laser light, and a fast digital video camera is preferred (e.g. IEEE 1394 FireWire or USB2). The scanning frequency (frames per second) depends on the hardware interface, i.e. the faster the system can transmit the video signals, the higher the frequency the equipment is able to grab, as well as on the selected image size. If e.g. a standard personal computer is used, such as a Pentium 4 having 1 GB RAM memory, 80 GB hard disk, operating with operating system Windows XP and furthermore having an Open GL graphical card and an IEEE 1394 FireWire interface, the grabbing frequencies vary between 15 Hz for an image size of 1280×1024 pixels and 40 Hz for an image size of 800×600 pixels. The pixel depth typically is of the order of 10-bit. Some examples of imaging body parts of human beings are given:

Example 1

Spine

Figure 10:
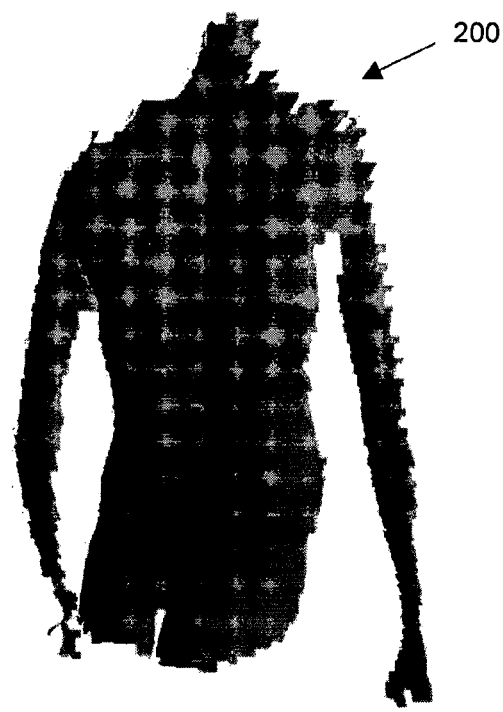
FIG. 10 is an illustration of the obtained measured surface, according to a method of the first embodiment of the present invention.
Figure 11:
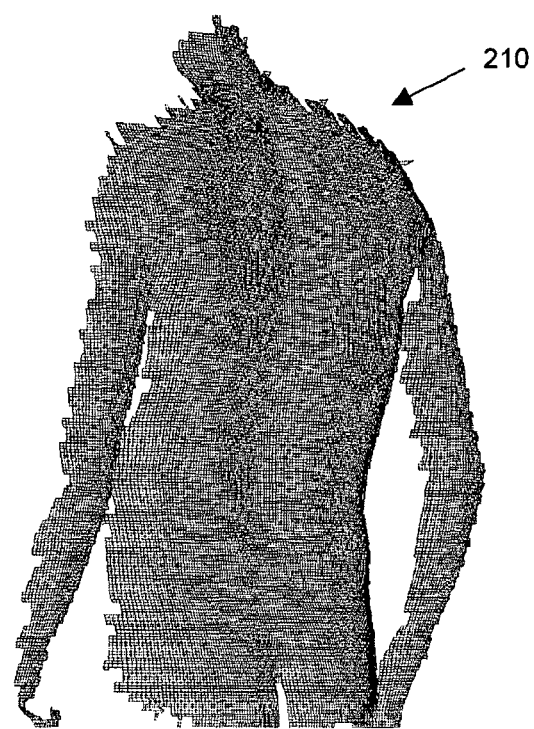
FIG. 11 is an illustration of the obtained regular grid describing the body surface, according to a method of the first embodiment of the present invention.

For the analysis of the spine, the back surface of a human body is captured in 4D, i.e. a 3-dimensional time dependent image, by projecting and capturing a set of horizontal raster lines on the back surface, as is illustrated in FIG. 4, by calculating the spatial coordinates of the lines for each frame as illustrated in FIG. 10, and by reconstructing the surface through a regular grid as illustrated in FIG. 11.

Example 2

Shoulder

For the analysis of the shoulder complex, the back and arm surfaces are captured as mentioned in example 1: by projecting horizontal raster lines from behind. Additional, the upper surface of both shoulders is captured by projecting a set of vertical raster lines from above and by capturing the surface with 2 additional video cameras with the equipment shown in FIG. 6, by calculating the spatial coordinates of the lines for each frame, and by reconstructing the surface through a regular grid.

Example 3

Pelvis

For the analysis of the pelvis, the buttocks and lower back surface is time-dependently captured in a series of three-dimensional images by projecting and capturing a set of horizontal raster lines on the surface, by calculating the spatial coordinates of the lines for each frame, and by reconstructing the surface through a regular grid.

Thus, in a preferred mode of the method 100 according to the present embodiment, structured light projection combined with raster line triangulation is used to record at least a part of the body surface as a function of time in three dimensions; active shapes and anatomical models trace and reconstruct the musculo-skeletal system of the scanned body parts time-dependently and three-dimensionally.

Alternative methods of obtaining surface information are included within the scope of the present invention. An example, is obtaining 3D surface information by means of a stereoscopic arrangement, i.e. using two cameras to obtain two slightly different images of the same scene and then analysing the two images to obtain a 3D representation of the object viewed.

Figure 12:
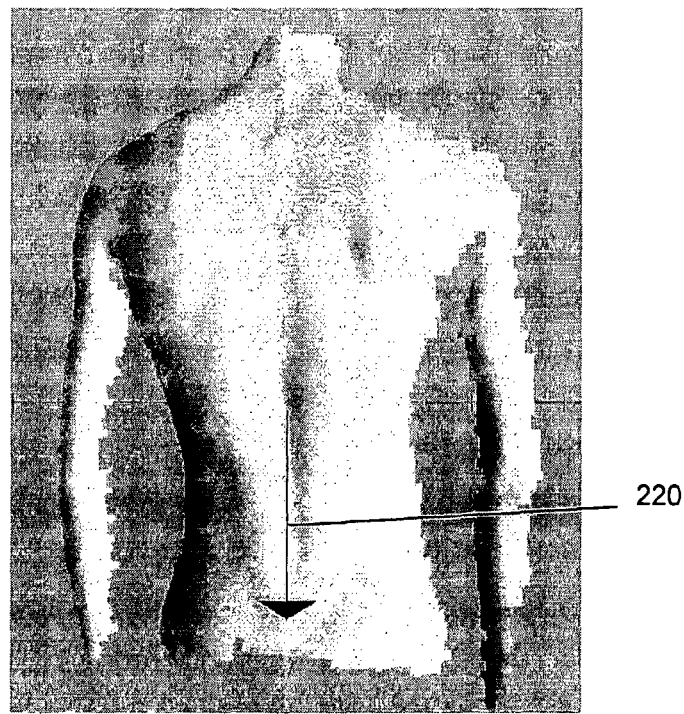
FIGS. 12 to 14 are an illustration of the results of feature tracing of the surface for part of a body based on the surface reconstruction as shown in FIGS. 10 and 11.
Figure 13:
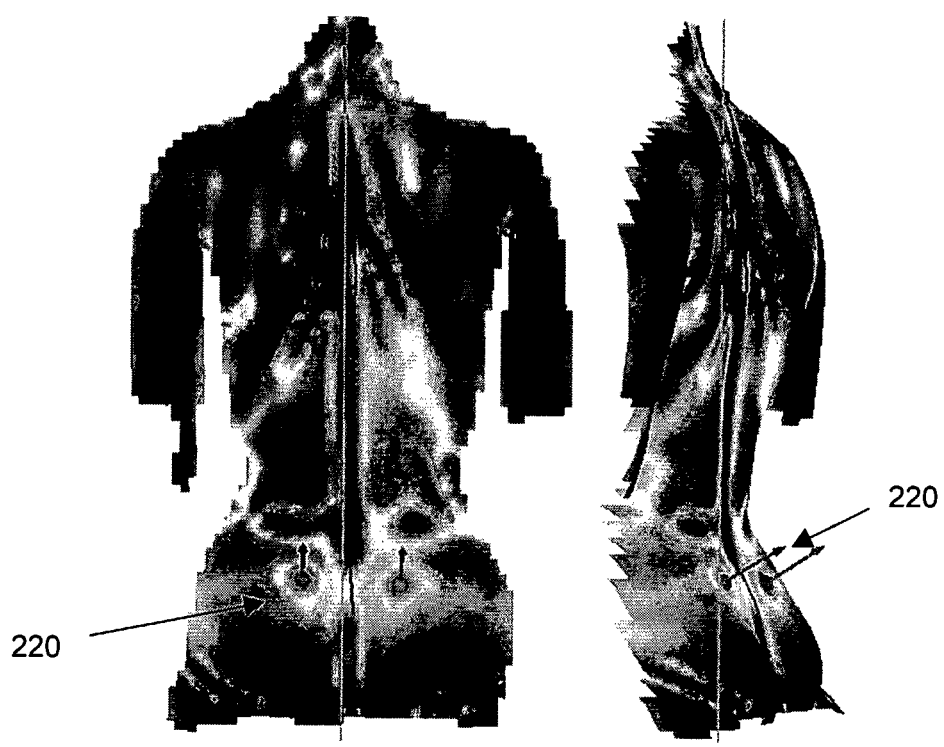
Figure 14:
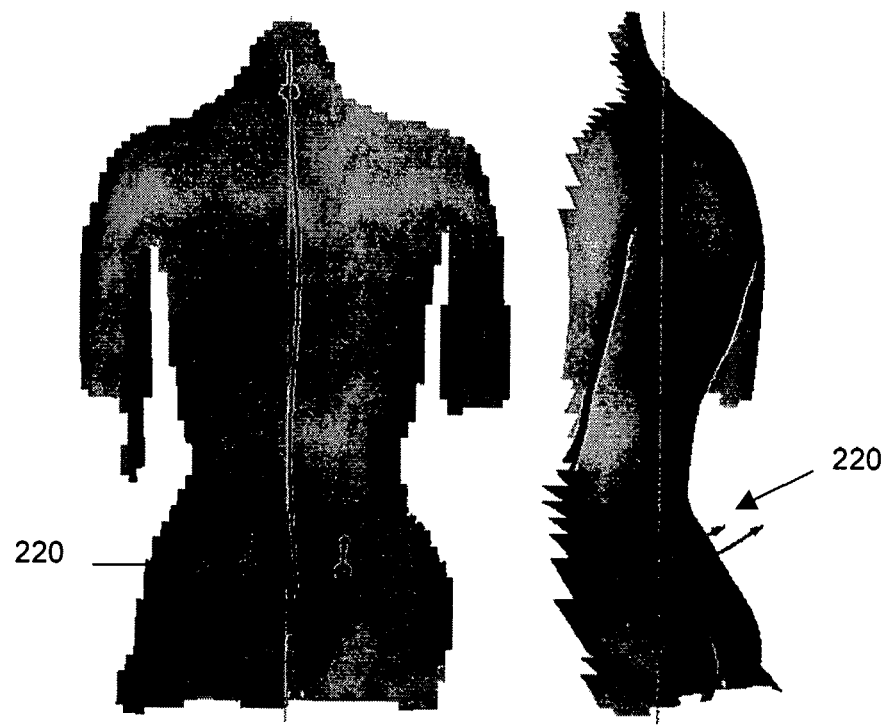

In a second step an invariant shape analysis extracts information consisting of points, areas, curves, objects and/or shapes that are anatomically relevant, e.g. the position of anatomical landmarks such as the sacrum point. In other words, anatomical surface information 220 is detected. Any suitable method of pattern recognition or image analysis can be used. As one example a specific (mathematical) "cost" may be defined in such a way that a minimisation of the cost leads to an optimal recognition of a well defined anatomical feature, e.g. the shape of the spine. Starting from an initial estimation, the point, contour, object or shape is moved iteratively over the image until the cost is minimized and appropriate properties are achieved. The cost of a point, contour, object or shape comprises two parts: an external cost and an internal cost. The external cost guides the point, contour, object or shape to a minimal cost position on the surface. The internal cost describes the internal behaviour of the point, contour, object or shape itself, e.g. to avoid results that are impossible from a biomechanical point of view. This technique may be described as a constrained cost optimisation technique. This technique is used to detect clinically relevant points, curves and shapes on the reconstructed three-dimensional time-dependent surface. The second step is illustrated in FIGS. 12 to 14 and is described in more detail in the following.

The second step of the method thus allows analysing the reconstructed surface, while taking into account the specific properties that characterise different parts of the human body, in order to detect and to follow anatomical surface information 220, i.e. clinically relevant features, on the reconstructed time-dependent three-dimensional surface in an automatic way, i.e. without the need to use markers.

For each body or body part a set of anatomical surface information 220, i.e. anatomical features, is defined, which is necessary and sufficient for the construction of a time-dependent three-dimensional personalised musculo-skeletal model of the body or body part. One suitable method is to extract the relevant features by defining a specific (mathematical) "cost" in such a way that a minimization of the cost leads to an optimal recognition of an anatomical feature, e.g. the shape of the spine. Starting from an initial estimation, the point(s), curve(s), object(s) and/or shape(s) related to at least part of a body are moved iteratively over the image until the cost is minimized and appropriate properties are achieved.

The cost of an active contour or shape may comprise two parts: an external cost and an internal cost. The external cost guides the point(s), contour(s), object(s) and/or shape(s) to a minimal cost position on the surface itself, based on surface properties such as curvature. The internal cost describes the internal behaviour of the point(s), contour(s), object(s) and/or shape(s) itself, also in relation to each other, e.g. to avoid results that are impossible from a biomechanical point of view. The combined technique may be described as a constrained cost optimisation technique. This technique is used to detect anatomical features, such as e.g. points, curves and shapes, on the reconstructed 4D surface, where each feature is characterised by a unique weighted average of the internal and external cost terms that are defined below.

External Cost Terms

Curvature

A first important entity is curvature, which is dependent on local image properties. The back surface for example has a high concavity at the position of the vertebral column, especially in the lumbar and sacral regions. In each point two perpendicular directions can be found where curvatures are extreme: the principal curvatures $\kappa_1$ and $\kappa_2$. Based on these principal curvatures two other curvatures can be defined, namely the Gaussian curvature $K=\kappa_1 \cdot \kappa_2$ and the mean curvature $H=\frac{1}{2}(\kappa_1+\kappa_2)$. The size and sign of these curvatures (e.g. sign of Gaussian curvature) enables the recognition of anatomical features such as e.g. the distinction of elliptic areas and hyperbolic areas on the surface.

Symmetry

For normal, healthy people the medial sagittal plane is a symmetry plane; this symmetry is manifested at the surface level, and can be used for the recognition of anatomical features that lie in this plane. Symmetry is applied by locating zones of minimal asymmetry: in each point P of the surface, the asymmetry function is defined by making a transversal cross section and by comparing the curvatures at points left and right of P. Based on the principal curvatures $\kappa_1$ and $\kappa_2$, the curvature in a arbitrary direction a can be calculated as $\kappa(\alpha)$, with $\alpha$ the angle in between the considered direction and the principal direction corresponding with the curvature $\kappa_1$. At the same distance from P two points $P_{left}$ and $P_{right}$ are defined at the left and at the right side of P; $\phi_{left}$ en $\phi_{right}$ are the angles in between the respective principal directions at these points and a transversal axis. Each curvature at $P_{left}$ making an angle $\alpha$ with the transversal axis has a mirror point $P_{right}$ making an angle $\pi-\alpha$ with the same axis. Curvatures left and right with corresponding directions are equal in case of perfect symmetry, and are calculated as follows:

$$\kappa_{left}(\alpha)=\kappa_1 \cos^2(\alpha-\phi_{left})+\kappa_2 \sin^2(\alpha-\phi_{left})$$

$$\kappa_{right}(\alpha)=\kappa_1 \cos^2(\pi-\alpha-\phi_{right})+\kappa_2 \sin^2(\pi-\alpha-\phi_{right})$$

Further the amount of asymmetry in between $P_{left}$ and $P_{right}$ can be calculated as the integral a (from 0 to $\pi$) of the square of the difference in between the corresponding curvatures. This integral represents the contribution of one couple of points. The total symmetry cost of P is the integral A of a over the entire transversal cross section, with b the width of the integration interval:

$$A = \frac{1}{b}\int a\, dx$$

Internal Cost Terms

Relative Position

Certain anatomical features (e.g. different parts of the shoulder complex) have a certain degree of freedom in which they can move with respect to each other. Depending on the body part that has to be modelled, the nature and range of these degrees of freedom are defined in internal cost terms in such a way that only plausible results are calculated.

An example is the relative height of the spinal bodies on the spinal mid-line compared with the anatomical detectable features C7, i.e. vertebra prominence, and L4, i.e. lumbal vertebra 4. The relative positions of the spinal bodies between C7 and L4 on the spinal curve are estimated from clinical publications and from statistical data collected from spinal x-rays. Also, the relative position of the spinal curve from the back surface is estimated from formulas that are extracted from sets of x-ray studies. The rotation of the spinal bodies are also constrained by the rotation of the spine as a whole and by the rotation of the body relative to the adjoining bodies; thus no vertebra is allowed to rotate "free", independent of its neighbours, and no vertebra is allowed to rotate to anatomical "impossible" positions. An "obvious" cost is that the bones are not allowed too close to the surface: they may not penetrate the skin. This constraint is implemented in all steps of the reconstruction, allowing false detections to be corrected in the iteration processes. Other relative-position constraints include the whole range of bone position relative to each other (left-right scapula relative to spine and clavicula, etc) and, as mentioned above, the degrees of freedom and movement range for the different joints.

Bending

In order to avoid results that are biomechanically, clinically or dynamically impossible, bending may be added as an internal cost. Including the bending of curves and shapes (or bending difference with a reference value) significantly improves the detection of anatomical features. With $\vec{s}(i)$ the natural parameterisation alongside a curve for example, and $\vec{s}(i)$ the 3D co-ordinate of a snake point for $2 \leq i \leq n-1$, the mathematical description of the bending vector difference is as follows:

$$|\vec{k}|_i = \sqrt{(|\vec{s}(i+1) - 2\vec{s}(i) + \vec{s}(i-1)| - bendingref_i)^2}$$

Torsion

Torsion—and the continuity of the torsion function alongside a curve or shape—may be included as an internal cost. In order to calculate the torsion at a certain curve or shape point $\vec{s}(i)$ with $2 \leq i \leq n-1$, the direction of the tangent lines to the curve in the points $\vec{s}(i-1)$ and $\vec{s}(i+1)$ is first calculated with a forward and backward differential respectively, being $\vec{t}(i-1) = \vec{s}(i) - \vec{s}(i-1)$ and $\vec{t}(i+1) = \vec{s}(i+1) - \vec{s}(i)$. The torsion $T(i)$ in the point $\vec{s}(i)$ can be calculated, starting from the normal $\vec{n}(i-1)$ and $\vec{n}(i+1)$ and the binormal in the surrounding points $\vec{s}(i-1)$ and $\vec{s}(i+1)$:

$$\vec{b}(i-1) = \vec{t}(i-1) \times \vec{n}(i-1) \text{ and } \vec{b}(i+1) = \vec{t}(i+1) \times \vec{n}(i+1)$$

$$\vec{T}(i) = \frac{\vec{b}(i+1) - \vec{b}(i-1)}{2}$$

Equidistance

During the calculations, points might mount up at places with a high curvature or symmetry, so that the bending and torsion will be minimized at these places. To avoid this effect an internal cost may be included to keep all points that describe a curve and/or shape at an equal distance.

Dynamical Properties

Because time-dependent measurements are performed, an extra internal cost can be added guiding the calculation of each new time frame by using prior knowledge on the motion. As an example, a Kalman filter can be used to predict the position of an anatomical feature in the analysed frame using the calculated position of the feature in the previous frame and the measurement of the frame. In this way it is possible to calculate positions of anatomical features that in some frames can not be reconstructed from the measurements only.

As an example, detection of anatomical relevant landmarks is described for the spine, the shoulder and the pelvis of a human body:

Example 1

Spine

For the analysis of the spine, active contours and shapes are used to locate the sacrum point, the dimple points and the vertebra prominens, and to trace the line through the processi spinosi. This is described in more detail by Kass et al. in International Journal of computer vision 1, p 321-331. At first, the sacrum point and the vertebra prominens are located as the beginning and the end point of the line through the spinous processes. The external cost is a weighted combination of the mean and Gaussian curvature.

Therefore the principle curvatures ($\kappa_1$, $\kappa_2$) are calculated in each point of the back shape. The sacrum point (SP) and vertebra prominens (VP) are located on the surface using a unique combination of the local maxima or minima in the mean and Gaussian curvature. The mean curvature (H) and the Gaussian curvature (K) are calculated as $$H = \frac{1}{2}(\kappa_1 + \kappa_2) \text{ and } K = \kappa_1 \cdot \kappa_2$$

The internal cost comprises the relative dynamic position of the sacrum point, the dimple points and the vertebra prominens with respect to each other.

Secondly, an active contour is introduced to locate the line through the spinous processes. An asymmetry function is used as a first external cost to calculate the minimal asymmetry point in each horizontal cross section. The entire profile of minimal asymmetry is found by connecting these symmetry points. In order to avoid results that are impossible from a biomechanical point of view, internal costs are added. First bending and torsion costs are included. These terms are related to the smoothness of the curve, preventing the curve from biomechanically impossible positioning. During the calculations, active contour points will mount up at places with high surface curvature and symmetry. To avoid this effect, a internal cost is included to keep all active contour points at an equal distance. Furthermore, an internal cost is added describing the observed biomechanical relation between the lateral deviation and the axial rotation of the vertebrae. The result is shown in FIG. 14.

Example 2

Shoulder

For the analysis of the shoulder complex, active contours and shapes are used to define the coordinates of the elbow, the coordinates of the acromion and the Margo Medialis on the scapula. Furthermore the direction of the upper arm, the scapula-thorax contact and the scapulohumeral rhythm are calculated in order to provide a set of anatomical features that is necessary and sufficient to build a personalized time-dependent three-dimensional model of the shoulder complex.

For the coordinates of the elbow the mean and Gaussian curvatures are external costs; the internal cost comprises the dynamic relative position with respect to the previously captured frame(s). For the coordinates of the acromion, the mean and Gaussian curvatures are external costs; the internal cost comprises the relative position with respect to other anatomical features, such as the position of the medial line (Margo Medialis) and the position of the humeral head.

The Margo Medialis is calculated by minimising a weighted average of external costs, e.g. the mean and Gaussian curvatures, and internal costs, such as e.g. the relative position with respect to other features, the height with respect to the entire image, the dynamic relative position with respect to the previously captured frame(s), and statistical information on its position from elbow measurements. For the direction of the upper arm, surface coordinates are defined as external cost, and the relative position with respect to other anatomical features is defined as internal cost. The scapula-thorax contact is based on the relative position of anatomical features, which is an internal cost. The scapulohumeral rhythm is based on statistical information on the position of the Margo Medialis from elbow and measurements, also an internal cost.

The calculations of the anatomical features of the shoulder complex are calculated in one single equation structure, which is necessary because different features are interrelated.

Example 3

Pelvis

For the analysis of the pelvis, the position of the dimple points is calculated. The external cost comprises a weighted combination of the mean and Gaussian curvature. The internal cost comprises the relative dynamic position of the dimple points with respect to other anatomical landmarks.

Figure 15:
FIGS. 15 to 16 are an illustration of the results of internal structure, such as a reconstruction of bony structures based on the information obtained during the feature tracing of the surface as shown in FIGS. 12 to 14.
Figure 16:
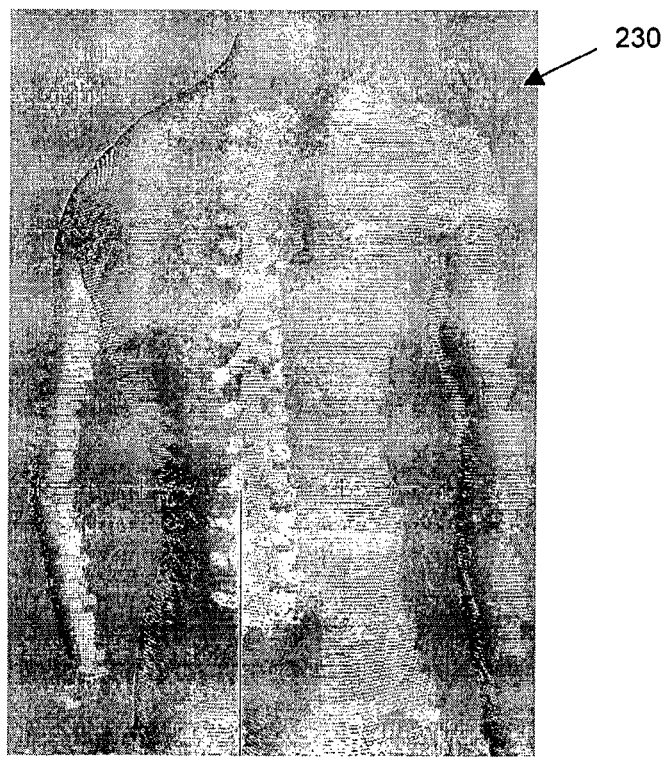
Figure 17:
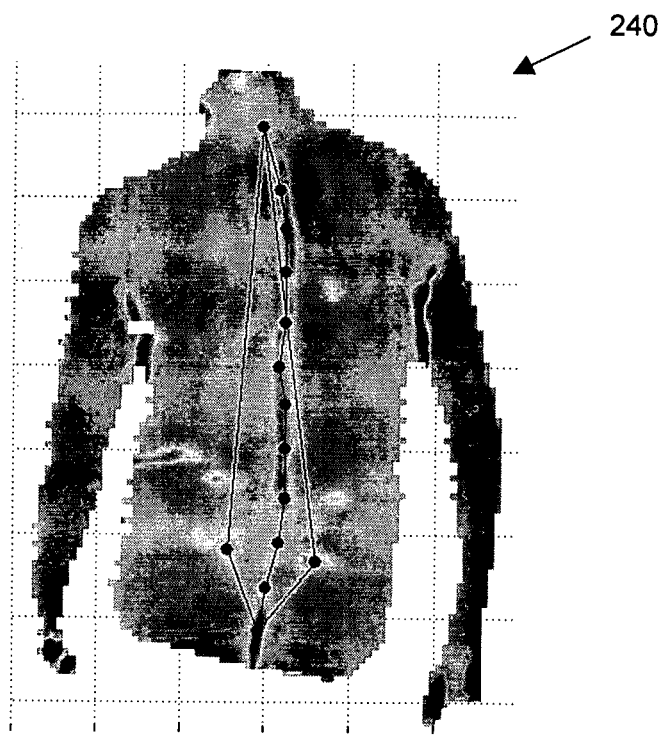
FIG. 17 to FIG. 19 illustrate images used for analysis of musculo-skeletal parameters based on the reconstruction of bony structures as shown in FIGS. 15 to 16.
Figure 18:
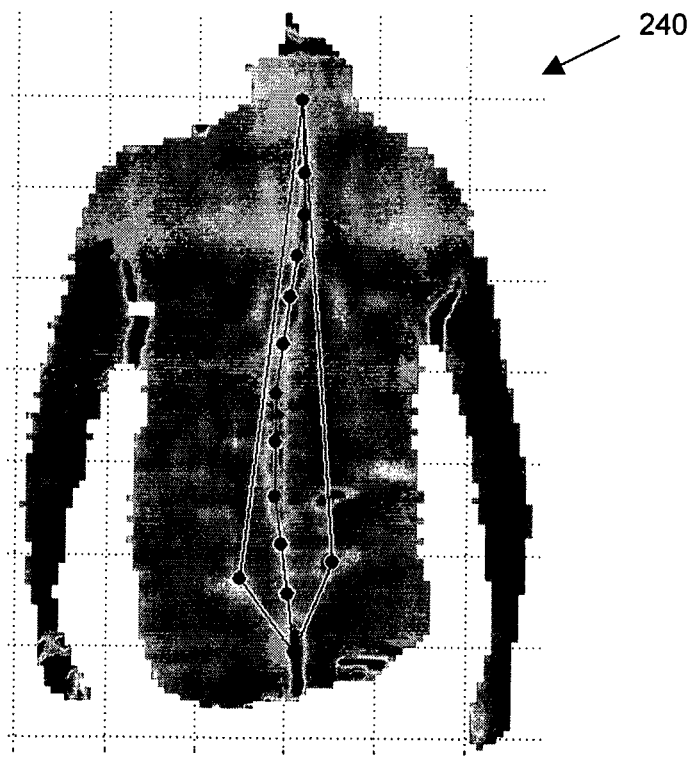
Figure 19:
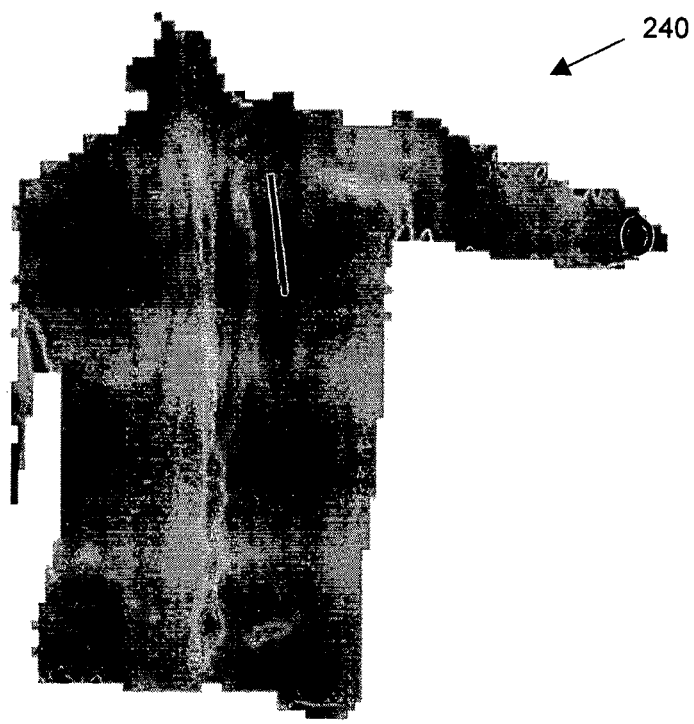

The third step comprises the reconstruction of an internal structure 230 e.g. a clinically relevant internal structure, e.g. bones, ligaments, tendons, muscles, as a function of time in three dimensions using bio-mechanical models of the human body, as illustrated on FIGS. 15 to 16. This reconstruction is based on the time-dependent three-dimensional information of the body surface itself and its anatomical surface information 220, e.g. positions of anatomical landmarks, which can be points, curves and/or surfaces, depending on the part of the human body that is scanned. Relevant kinetic and kinematic parameters are then extracted from the data in order to analyse and visualize body movements, constraints and dynamics. The models allow measurements of e.g. the shape of the spine, the leg axis, foot disorders. Thanks to the plenitude of information (anatomical points, curves and surfaces), the time-dependent three-dimensional model is personalised to a much higher degree than models using only marker positions. The matching of the frames (to obtain dynamic measurements) takes place with the obtained model from the previous step. In order to make a maximal use of the information from the successive images, a combination of mathematical and statistical methods is used, e.g. a Kalman filter, which is a set of mathematical equations that provides an efficient computational (recursive) solution of the least-squares method. As a result, skeletal movements, joint moments and muscle strengths can be analysed as a function of time in three dimensions as illustrated on FIGS. 17 to 19. In this way a personalised musculo-skeletal model 240 is obtained. In addition, the personalised musculo-skeletal model 240 can be animated. Thanks to the fact that anatomical points, curves and surfaces are measured together as a function of time, the model is able to incorporate a self-checking feature. Positions and/or movements that are impossible from a biomechanical or anatomical point of view can be excluded and/or adjusted, e.g. in such a way that specific (parts of) bones or muscles have a certain time-dependent position with respect to the body surface, and in such a way that movement of these parts occurs at speeds that are plausible from a biomechanical or anatomical point of view. Other techniques cannot have this self-checking ability, as they do not dispose of time-dependent information (e.g. X-rays) or curve/surface information (e.g. measuring techniques using markers).

Example 1

Spine

The internal spine is reconstructed from the external spine using an anatomical formula, estimating the distance of the skin to the centre of a vertebral body, as illustrated on FIGS. 15 and 16. Spinal parameters (e.g. lumbar lordisis angle) can be monitored as a function of time in three dimensions. A detailed deduction of the anatomical formula is described by Drerup et al. in Clinical Biomechanics 9 p 28-36.

Example 2

Shoulder

Figure 20:
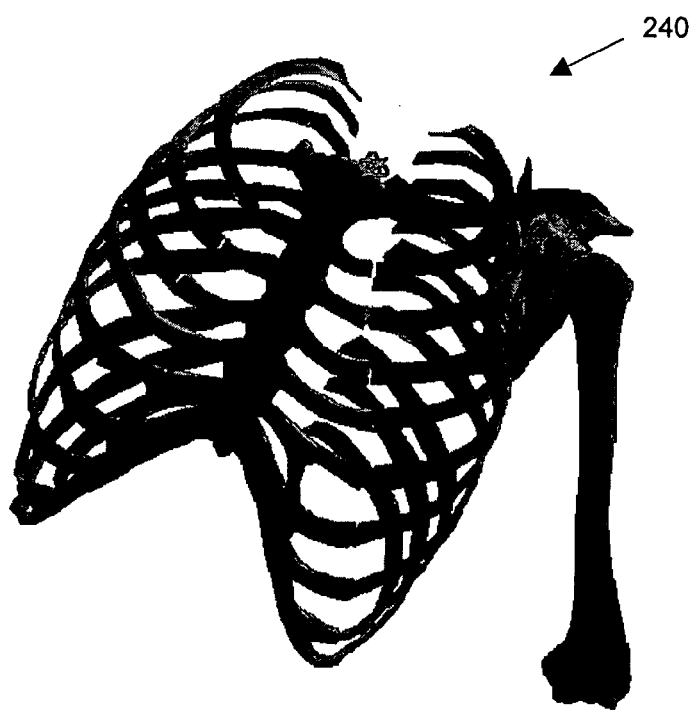
FIG. 20 is an illustration of the reconstruction of bony structures for a shoulder of a human body according to an embodiment of the present invention.

The shoulder is a complex joints and it is not possible to model it as a 3 degrees-of-freedom spherical joint. The skeletal model 240, as shown in FIG. 20, contains the following bones: the sternum, clavicula, scapula and humerus. Between the bones, three joints have been defined: the sternoclavicular joint, the acromioclavicular joint and the glenohumeral joint. These joints are modelled as three-degrees-of-freedom (DOFs) spherical joints. The scapulothoracic joint is modelled in such a way that the scapula is able to move freely with respect to the thoracic wall, in order to enable winging. The set of measured anatomical features is necessary and sufficient to define all DOF's of the system, and to build a personalised time-dependent three-dimensional model of the shoulder complex.

Example 3

Pelvis

A personalised time-dependent three-dimensional model of the pelvis is reconstructed from the lower back surface and the position of the dimple points.

Figure 21:
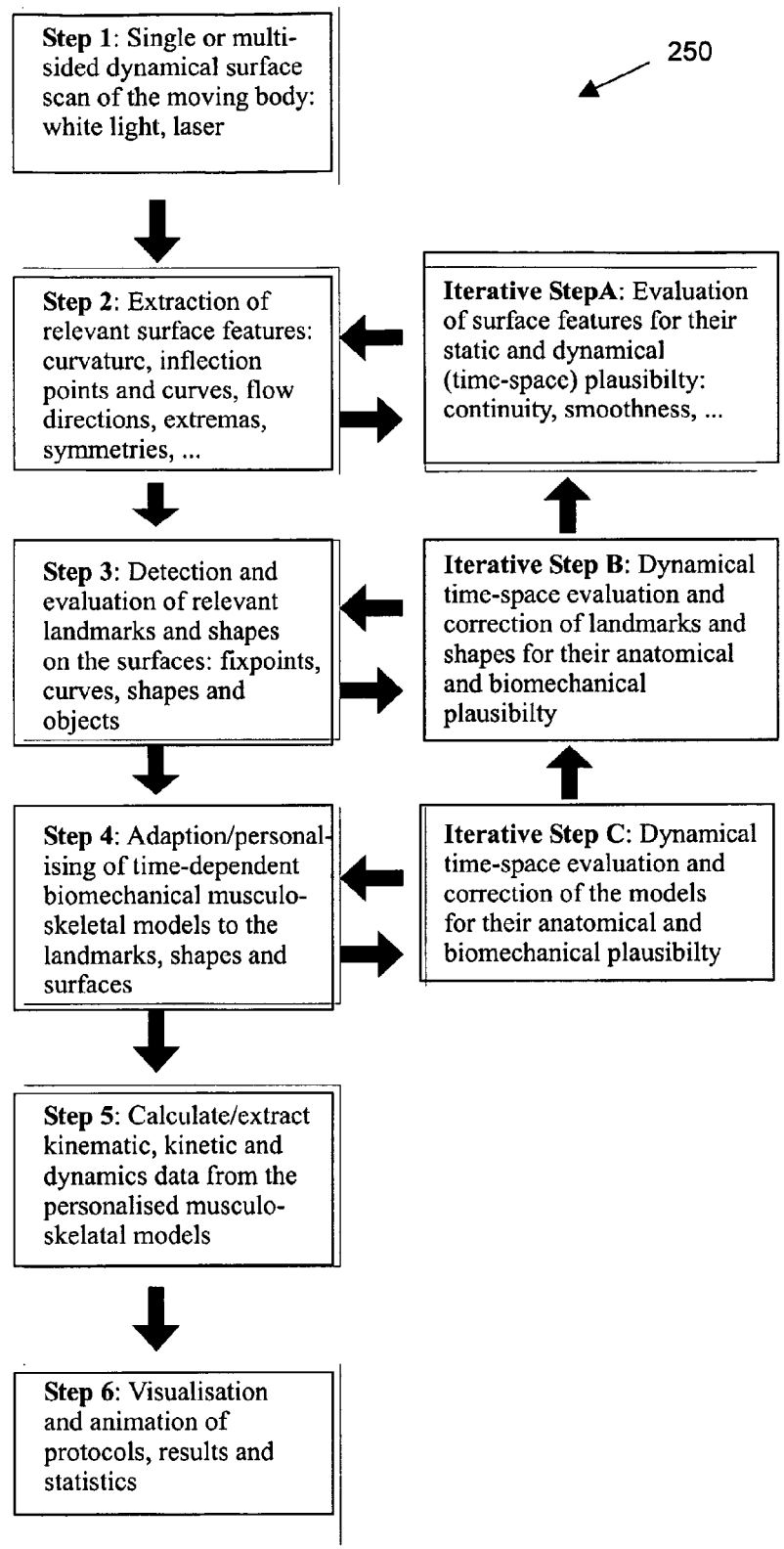
FIG. 21 shows a flowchart of the method used for construction of a musculo-skeletal model for parts of a body according to an embodiment the present invention.

In conclusion, the method of the above described embodiment comprises the provision, e.g. grabbing, of surface images of a moving body by suitable scanning or projection equipment, e.g. optical equipment. Thereby either a one-sided surface (like human back, face, . . . ) or a multi-sided surface (legs, torso, . . . ) is recorded. The method furthermore comprises the reconstruction and mapping on a regular grid of the surface, thus giving a sequence of single static surfaces. On the regular surfaces, invariant features are calculated, like curvature and symmetry and invariant features are used for detecting anatomical landmarks and shapes on each of the static surface, like vertebra prominence, sacrum point (rima ani), left and right dimples, acromium, scapula, spinal symmetry line (processi spinosi). In the next step, the landmarks and shapes are dynamically verified on the sequence, thus producing a time dependent set of landmarks and shapes and finally, the biomechanical models are adapted to the dynamic set of landmarks, resulting in a personalised musculo-skeletal model. This process is illustrated in FIG. 21 by method 250.

A further embodiment of the present invention relates to the method of performing detection of anatomical surface information, such as e.g. time-dependent landmarks based on time-dependent three dimensional images of a surface as described in the second step of the first embodiment. This method of detection of time dependent landmarks can be used in a wide variety of applications and thus is not restricted to the specific use in the first embodiment, restricted to musculo-skeletal models. In other words, the method for detecting time-dependent landmarks on a surface based on the topography of a surface of a part or parts of a body of a creature in a series of time dependent images of that surface is an independent invention. The specific features of this method are identical to the features described in step two of the first embodiment of the present invention. Defining the costs as described in step two of the first embodiment allows to obtain an efficient way of detecting time dependent landmarks. It is an advantage of the current embodiment that it uses not only point information but also shape information of the surface. This also allows to detect anatomical landmarks in a more efficient way, compared to methods for detecting landmarks that are known from the prior art.

Another embodiment of the current invention relates to the actual building of a time-dependent three-dimensional musculo-skeletal model, as described in the third step of the first embodiment. This method is not restricted to a specific imaging technique or to a specific method of obtaining the anatomical surface information but is an independent invention. The features of the method for building a time-dependent three-dimensional musculo-skeletal model are the same as those described in the third step of the first embodiment of the present invention. It is a specific advantage of the present embodiment that it uses the obtained anatomical surface information to create a set of boundary conditions for a biomechanical model and that the mechanical model is build according to those boundary conditions. The method of the current embodiment furthermore includes the checking whether the model fulfils these boundary conditions during further dynamical development of the bodies, i.e. during further movement and thus during dynamical changes of the model for musculo-skeletal structure. The latter allows to biomechanically correct modelling of part or parts of the body of a creature.

In accordance with further embodiments, the present invention includes a computer program product which provides the functionality of any of the methods according to the present invention when executed on a computing device. Further, the present invention includes a data carrier such as a CD-ROM or a diskette which stores the computer product in a machine-readable form and which executes at least one of the methods of the invention when executed on a computing device. Nowadays, such software is often offered on the Internet, hence the present invention includes transmitting the computer product according to the present invention over a local or wide area network. The computing device may include a personal computer or a workstation. The computing device may include one of a microprocessor and an FPGA.

Figure 22:
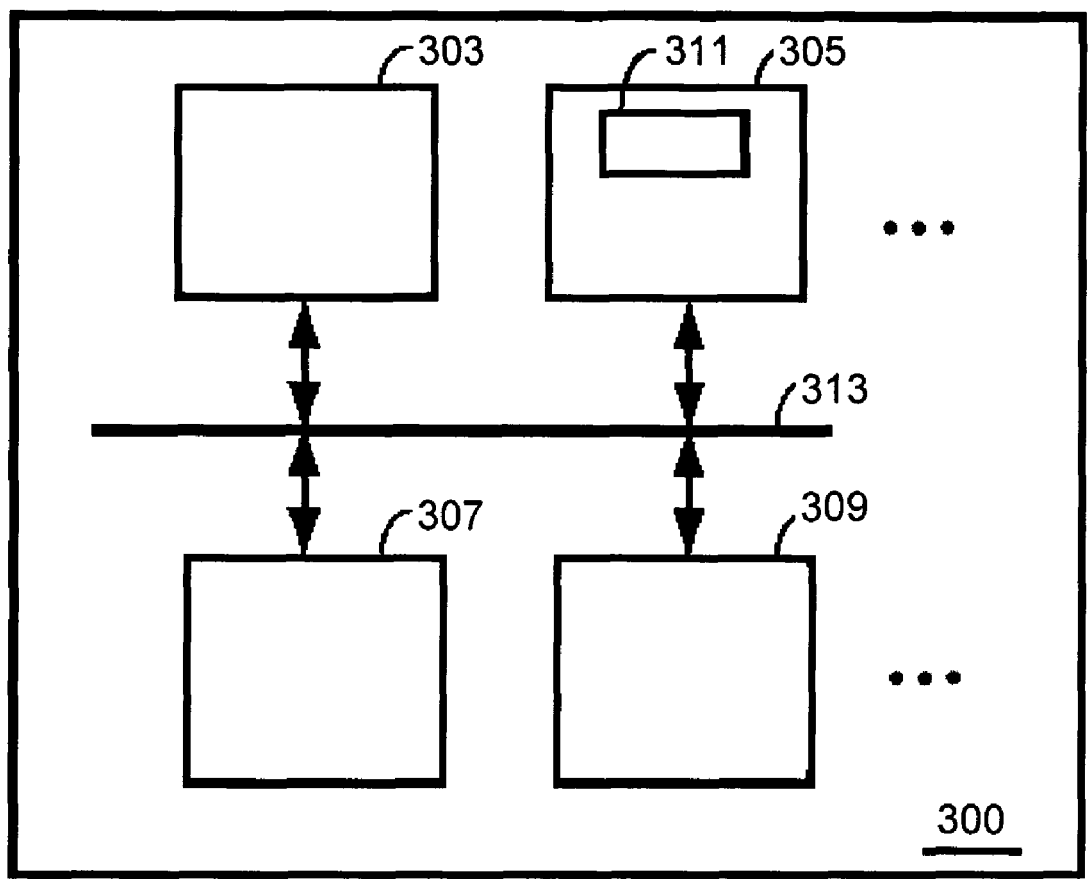
FIG. 22 illustrates a computing means adapted for performing computational parts of any of the methods as described in accordance with embodiments of the present invention.

The above invention or one or more aspects thereof described in the embodiments may be at least partly implemented in a processing system 300 such as shown in FIG. 22. FIG. 22 shows one configuration of processing system 300 that includes at least one programmable processor 303 coupled to a memory subsystem 305 that includes at least one form of memory, e.g., RAM, ROM, and so forth. A storage subsystem 307 may be included that has at least one disk drive and/or CD-ROM drive and/or DVD drive. In some implementations, a display system, a keyboard, and a pointing device may be included as part of a user interface subsystem 309 to provide for a user to manually input information. Ports for inputting and outputting data also may be included. More elements such as network connections, interfaces to various devices, and so forth, may be included, but are not illustrated in FIG. 22. The various elements of the processing system 300 may be coupled in various ways, including via a bus subsystem 313 shown in FIG. 22 for simplicity as a single bus, but will be understood to those in the art to include a system of at least one bus. The memory of the memory subsystem 305 may at some time hold part or all (in either case shown as 311) of a set of instructions that when executed on the processing system 300 implement the step(s) of the method embodiments described herein. Thus, while a processing system 300 such as shown in FIG. 22 is prior art, a system that includes the instructions to implement aspects of the present invention and/or computational parts thereof is not prior art, and therefore FIG. 22 is not labeled as prior art.

It is to be noted that the processor 303 or processors may be a general purpose, or a special purpose processor, and may be for inclusion in a device, e.g., a chip that has other components that perform other functions. Processor 303 may include a computing device, e.g. microprocessor, for instance it may be a micro-controller. In particular, it may be a programmable controller, for instance a programmable digital logic device such as a Programmable Logic Array (PLA), a Programmable Array Logic (PAL), a Programmable Gate Array, especially a Field Programmable Gate Array (FPGA). Thus, one or more aspects of the present invention can be implemented in digital electronic circuitry, or in computer hardware, firmware, software, or in combinations of them. Furthermore, as described above, aspects of the invention or the computational parts thereof can be implemented in a computer program product tangibly embodied in a carrier medium carrying machine-readable code for execution by a programmable processor. Method steps of aspects of the invention may be performed by a programmable processor executing instructions to perform functions of those aspects of the invention, e.g., by operating on input data and generating output data.

Other arrangements for accomplishing the objectives of the method and system embodying the invention will be obvious for those skilled in the art. It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. A computer based method for detecting and/or extracting from a series of time-dependent images of a surface of body parts of a creature anatomical features on surface measurements, said method comprising using invariant feature analysis to determine anatomical landmarks and shapes using said computer, wherein said invariant feature analysis comprises using said computer to fulfill predetermined conditions describing topographic characteristics of the surface of the body parts of the creature and using said computer to fulfill predetermined conditions describing topographic, topologic and/or volumetric characteristics of the interior of the body parts of the creature, and wherein said topographic characteristics of the surface of the body parts of the creature are curvature and symmetry of surface parts of the body parts of the creature and said topographic, topologic and/or volumetric characteristics of the interior of the body parts of a creature are the relative position, bending, torsion, equidistance and dynamical properties of interior parts of the body parts of the creature.

2. The method according to claim 1, wherein said predetermined conditions describing topographic characteristics of the surface of the body parts of the creature and said predetermined conditions describing topographic, topologic and volumetric characteristics of the interior of the body parts of the creature are determined by biomechanical constraints.

3. The method according to claim 1, wherein said invariant feature analysis comprises active contour modelling.

4. The method according to claim 3, wherein said active contour modelling is based on optimising a finite number of active contour points, all said active contour points substantially being at an equal distance.

5. The method according to claim 1, wherein said invariant feature analysis comprises active shape modelling.

6. A computer program product comprising a non-transitory computer readable medium comprising a computer-readable program code embodied therein, said code adapted to be executed to implement the method as claimed in claim 1.

7. A machine readable data storage device storing the computer program product of claim 6.

8. A computer program product comprising a comprising a non-transitory computer readable medium comprising a computer-readable program code embodied therein, said code adapted to be executed to implement the method as claimed in claim 3.

9. A machine readable data storage device storing the computer program product of claim 8.

* * * * *